US012012592B2

(12) United States Patent
Park et al.

(10) Patent No.: US 12,012,592 B2
(45) Date of Patent: Jun. 18, 2024

(54) TARGET MATERIAL EXTRACTION APPARATUS WITH REPLACEMENT OF MAGNETIC BAR BLOCK ALLOWED

(71) Applicant: BIONEER CORPORATION, Daejeon (KR)

(72) Inventors: Han-Oh Park, Sejong-si (KR); Min Sung Kook, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 785 days.

(21) Appl. No.: 17/262,796

(22) PCT Filed: Jul. 23, 2019

(86) PCT No.: PCT/KR2019/009076
§ 371 (c)(1),
(2) Date: Jan. 25, 2021

(87) PCT Pub. No.: WO2020/022742
PCT Pub. Date: Jan. 30, 2020

(65) Prior Publication Data
US 2021/0230579 A1  Jul. 29, 2021

(30) Foreign Application Priority Data
Jul. 26, 2018  (KR) ........................ 10-2018-0087415

(51) Int. Cl.
*C12N 15/10* (2006.01)
*B01L 3/00* (2006.01)
(52) U.S. Cl.
CPC ........ *C12N 15/1006* (2013.01); *B01L 3/5088* (2013.01); *B01L 2200/02* (2013.01); *B01L 2300/0829* (2013.01); *B01L 2400/043* (2013.01)

(58) Field of Classification Search
CPC .................................................. C12N 15/1006
See application file for complete search history.

(56) References Cited

U.S. PATENT DOCUMENTS 3,970,518 A   7/1976  Giaever
3,985,649 A  10/1976  Eddelman
(Continued)

FOREIGN PATENT DOCUMENTS

CN   103210077 A   7/2013
CN   203174009 U   9/2013
(Continued)

OTHER PUBLICATIONS

Notice of Allowance issued in counterpart Japanese Patent Application No. 2021504469 on Sep. 30, 2022.
(Continued)

*Primary Examiner* — Jill A Warden
*Assistant Examiner* — Alex Ramirez
(74) *Attorney, Agent, or Firm* — HULTQUIST, PLLC; Steven J. Hultquist

(57) ABSTRACT

The present invention relates to an extraction apparatus capable of simultaneously extracting target materials from multiple biological samples and, more particularly, to a target material extraction apparatus in which magnetic bar blocks can be replaced according to kinds of multi-well plates to be inserted into a cartridge. When used, the target material extraction apparatus of the present invention is operated in such a manner that among various plates multi-well having different numbers of wells, multi-well plates suitable for a use purpose are loaded into a cartridge within the apparatus and magnetic bar blocks equipped with magnetic bars suitable therefor are selected and loaded. Thus, the apparatus has the advantage of selectively applying various multi-well plates to one installment according to the number (Continued)

of samples from which a target material is extracted or to the amount of the target material to be extracted.

6 Claims, 3 Drawing Sheets

(56) References Cited

U.S. PATENT DOCUMENTS

| | | | |
|---|---|---|---|
| 5,558,839 A | 9/1996 | Matte et al. | |
| 5,567,326 A | 10/1996 | Ekenberg et al. | |
| 5,770,461 A | 6/1998 | Sakazume et al. | |
| 5,897,783 A | 4/1999 | Howe et al. | |
| 6,040,192 A | 3/2000 | Tuunanan | |
| 6,468,810 B1 | 10/2002 | Korpela | |
| 2003/0127396 A1 | 7/2003 | Siddiqi | |
| 2008/0308500 A1* | 12/2008 | Brassard | B03C 1/06 210/695 |
| 2010/0136563 A1 | 6/2010 | Keller et al. | |
| 2010/0200405 A1 | 8/2010 | Lenz et al. | |
| 2011/0009608 A1 | 1/2011 | Kim et al. | |
| 2012/0058479 A1 | 3/2012 | Gisler et al. | |
| 2013/0230860 A1* | 9/2013 | Park | B01L 3/0227 435/6.12 |
| 2015/0031037 A1 | 1/2015 | Li et al. | |
| 2016/0054340 A1 | 2/2016 | Gisler et al. | |
| 2016/0161517 A1 | 6/2016 | Gisler et al. | |

FOREIGN PATENT DOCUMENTS

| | | |
|---|---|---|
| CN | 103923163 | 5/2017 |
| CN | 103923163 B | 5/2017 |
| CN | 107345199 A | 11/2017 |
| CN | 206956049 U | 2/2018 |
| JP | 1068731 A | 3/1998 |
| JP | 2010172824 A | 8/2010 |
| JP | 2011234671 A | 11/2011 |
| JP | 2014524262 A | 9/2014 |
| JP | 2017502653 A | 1/2017 |
| KR | 100483684 B1 | 4/2005 |
| KR | 100720044 B1 | 5/2007 |
| KR | 20070086879 A | 8/2007 |
| KR | 1020110121588 A | 11/2011 |
| KR | 1020220121588 A | 11/2011 |
| WO | 9626011 | 8/1996 |
| WO | 2015062549 A1 | 5/2015 |

OTHER PUBLICATIONS

English Translation of Notice of Allowance issued in counterpart Japanese Patent Application No. 2021504469 on Sep. 30, 2022.
Office Action issued in counterpart European Patent Application No. 19839951.1 on Oct. 25, 2022.
Office Action issued on Dec. 29, 2023 for Chinese Patent Application No. 201980055502.5.
English translation of Office Action issued on Dec. 29, 2023 for Chinese Patent Application No. 201980055502.5.
Search Report issued on Dec. 28, 2023 for the Chinese Patent Application No. 201980055502.5.

* cited by examiner

TARGET MATERIAL EXTRACTION APPARATUS WITH REPLACEMENT OF MAGNETIC BAR BLOCK ALLOWED

CROSS-REFERENCE TO RELATED APPLICATIONS

This is a U.S. national phase under 35 USC § 371 of International Patent Application No. PCT/KR2019/009076 filed Jul. 23, 2019, which in turn claims priority under 35 USC § 119 of Korean Patent Application No. 10-2018-0087415 filed Jul. 26, 2018. The disclosures of International Patent Application No. PCT/KR2019/009076 and Korean Patent Application No. 10-2018-0087415 are hereby incorporated herein by reference in their respective entireties, for all purposes.

TECHNICAL FIELD

The present invention relates to an extraction apparatus capable of simultaneously extracting a target material from multiple biological samples, and more particularly to an apparatus for extracting target material wherein a magnetic bar block can be replaced according to the kind of a multi-well plate to be inserted into a cartridge.

BACKGROUND ART

Various methods of separating nucleic acid, protein, etc. from a biological sample have been developed. Conventionally, a precipitation method, a liquid extraction method, an electrophoretic method, a chromatographic method, and the like were used. In order to more simply perform manipulation, however, a solid extraction method has been developed.

The solid phase extraction method is a method of using a solid having selectivity or using solid particles manufactured by attaching a ligand having high selectivity to a solid. The solid extraction method is performed based on the principle of dissolving a biological sample in a solution to which a target material is selectively attached first, attaching the target material to a solid, separating the solid from the solution, washing the residual material on the solid off to remove other impurities, and separating a desired target material from the solid.

In the case in which the solid extraction method is used to fill a column with solid particles or to fill the column with a filter film, the solution slowly flows between micropores, whereby much time is required to separate the target material. A method of using centrifugation may be used in order to solve this problem. However, it is difficult to automate this method. In the case in which pressurization or vacuum is used, there is a problem in that, upon application to a plurality of samples, results obtained from the samples are not uniform due to a difference in solution flow speed between the samples.

In order to solve this problem, technology for attaching a target material in a suspension state of a solution using fine magnetic particles having large surface area, applying a magnetic field to agglutinate the magnetic particles having the target material attached thereto, and removing the solution to separate the target material (U.S. Pat. Nos. 3,970,518 and 3,985,649).

A method of separating a target material using magnetic particles is mainly divided into a target material attachment step, a solution removal and washing step, and a target material detachment step. The target material attachment step is a method of uniformly suspending magnetic particles to agglutinate the magnetic particles, wherein a magnetic field is basically used in order to agglutinate the magnetic particles. The magnetic field is generated by a permanent magnet or an electromagnet. In general, the permanent magnet is capable of generating a strong magnetic field without emission of heat, unlike the electromagnet. However, magnetic flux of the permanent magnet cannot be switched on and off, unlike the electromagnet. For this reason, a magnetic particle solution must be physically moved between the magnets for switching, whereby the permanent magnet is disadvantageous in automation.

The position at which the magnetic particles are agglutinated is changed depending on the position to which the magnetic field is applied. The position at which the magnetic particles are agglutinated is important to efficiently remove the solution, and therefore technologies related to the position have been developed. Separation apparatuses using magnetic particles have been developed so as to be widely applied to diagnostic test equipment and nucleic acid extraction equipment mainly using antigen-antibody reaction. A method of agglutinating magnetic particles on the bottom of a 96-well plate and then suspending the magnetic particles has been developed by Pasteur Sanofi Diagnostics (U.S. Pat. No. 5,558,839). However, this method has a problem in that the magnetic particles on the bottom are lost when the solution is completely removed. In order to solve this problem, a method of locating a magnet at the side surface of a vessel, rotating the magnet or the vessel to suspend magnetic particles, and stopping the rotation of the magnet or the vessel to agglutinate the magnetic particles to the surface of a wall has been developed (WO 96/26011), and a system capable of performing agglutination and suspension using a uniform magnetic field and an alternating magnetic field has been developed by Hitachi (U.S. Pat. No. 5,770,461). This method is a method of attaching magnetic particles to the surface of a wall of a tube a uniform magnetic field to agglutinate and wash the magnetic particles and suspending the magnetic particles using an alternating magnetic field. A system for moving a doughnut-shaped magnet in a direction perpendicular to a vessel to switch a magnetic field has been developed by Amersham International plc (U.S. Pat. No. 5,897,783). This is a method of agglutinating magnetic particles on the inner wall of a tube in a circular shape. All of these methods are methods of agglutinating magnetic particles in a reaction vessel, removing a solution, pouring a new solution, and suspending the magnetic particles again.

In contrast to these methods, a method of moving magnetic particles inside reaction vessels containing solutions to suspend the magnetic particles and moving the magnetic particles again has been developed by Labsystems. This system includes bars capable of performing upward-downward movement like a fishing rod and a bar case. A permanent magnet is installed at the lower end of the bars, and the bar case is made of plastic, which transmits magnetic force, and seals the bars such that the bars do not contact the solution (U.S. Pat. No. 6,040,192). The operation thereof is performed as follows: the bar case is introduced into a reaction solution in the state in which the magnetic bar is withdrawn from the bar case, the bar case is moved upwards and downwards to suspend magnetic particles such that the magnetic particles react, the magnetic bar is completely inserted into the bar case, and the magnetic particles are agglutinated on the surface of the magnetic bar case by a magnetic field of the magnetic bar, whereby a desired target material is attached to the magnetic particles. Subsequently, the magnetic particles having the target material attached thereto may be moved to the next solution together with the magnetic bar and the bar case. After moving, the magnetic bar is withdrawn from the bar case, the magnetic field is removed, and the bar case is moved upwards and downwards to suspend the agglutinated magnetic particles in the new solution. An automatic nucleic acid extractor having the same operation scheme as the above has been developed by BIONEX (Korean Registered Patent No. 10-0483684). This is a system for attaching magnetic particles to a bar case in which various magnetic bars are inserted, moving the magnetic particles to another solution such that the magnetic particles are suspended in the solution to extract nucleic acid in the same manner as in the above U.S. '192 patent. However, both the technology of Labsystems and the technology of BIONEX process samples arranged in a line, whereby there is limitation in processing a plurality of samples. For this reason, technology for using magnetic bars disposed in a two-dimensional array in automatic extraction equipment for processing a plurality of samples, such as samples contained in a 96-well plate, has been developed by Core Bio System (Korean Patent No. 10-0720044).

However, the magnetic bar is manufactured in the form of a block including 96 magnetic bars disposed in a two-dimensional array so as to be suitable for a 96-well plate kit, and therefore there is a problem in that the 96-well plate must always be used irrespective of the number of biological samples and the amount of a target material to be extracted.

In the present invention, in order to solve the above problem, an apparatus configured such that, in the case in which a target material is simultaneously extracted from a plurality of biological samples, various kinds of multi-well plates, i.e. cartridges for dispensing the samples, are selectively used depending on the number of the biological samples or the amount of the target material to be extracted has been developed. To this end, a method of replacing a magnetic bar block in order to adjust the number of magnetic bars so as to be suitable for the number of wells of a cartridge has been developed, whereby it is possible to efficiently extract a target material using a single apparatus depending on the number of biological samples and the amount of a target material to be extracted.

DISCLOSURE

Technical Problem

It is an object of the present invention to provide an apparatus for extracting a target material configured such that a multi-well plate suitable for purpose of use is selected for replacement and mounted from among various kinds of multi-well plates having different numbers of wells in order to extract a target material.

Technical Solution

In order to accomplish the above object, the present invention provides an apparatus for extracting a target material comprising a magnetic bar block replacement unit (100) comprising:
- a magnetic bar block (110) having a magnetic bar (111) configured to be introduced into each well of a multi-well plate so as to be operated;
- a magnetic bar block holder (120) configured to allow the magnetic bar block (110) to be mounted thereto; and
- a fixing member (130) configured to fix the magnetic bar block (110) to the magnetic bar block holder (120).

BEST MODE

The present invention proposes a method of extracting a target material using an apparatus for extracting target material irrespective of the kind of a multi-well plate in which biological samples are dispensed or the kind of a cartridge in which the multi-well plate is mounted. As a means therefor, the present invention proposes an apparatus for extracting target material configured such that a multi-well plate suitable for purpose of use is selected for replacement and mounted from among various kinds of multi-well plates having different numbers of wells in order to extract a target material and correspondingly a magnetic bar block having a magnetic bar configured to be introduced into each well of the multi-well plate so as to be operated is selected for replacement and mounted. The apparatus for extracting target material according to the present invention is characterized in that various kinds of multi-well plates and various kinds of magnetic bar blocks having magnetic bars suitable therefor are provided together, whereby it is possible to appropriately select and apply a multi-well plate to one piece of equipment depending on the number of samples to be extracted or the amount of a target material to be extracted.

Hereinafter, an embodiment of the present invention will be described in detail with reference to the accompanying drawings.

Figure 1:
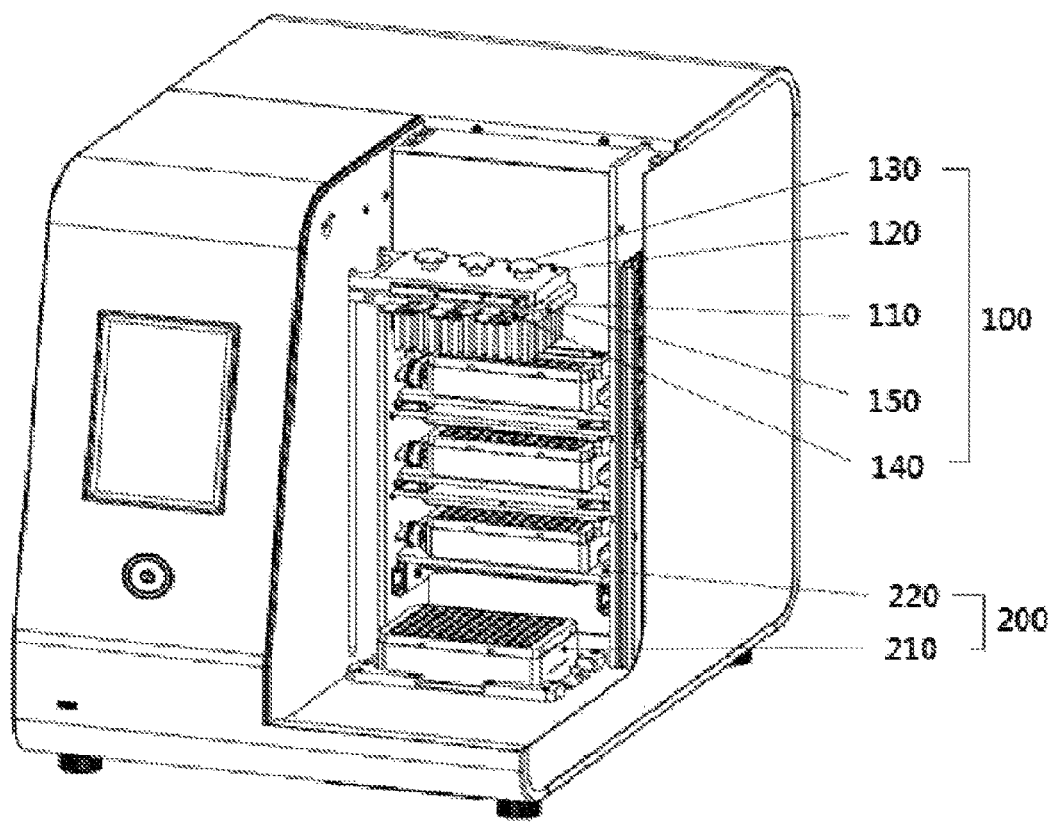
FIG. 1 is a perspective view of an apparatus for extracting target material according to an embodiment of the present invention.

FIG. 1 is a perspective view of an apparatus for extracting target material according to an embodiment of the present invention.

According to the embodiment of the present invention, the apparatus for extracting target material includes a magnetic bar block replacement unit 100 and a cartridge mounting unit 200.

In the present invention, the magnetic bar block replacement unit 100 includes a magnetic bar block 110 having a magnetic bar 111 configured to be introduced into each well of a multi-well plate so as to be operated, a magnetic bar block holder 120 configured to allow the magnetic bar block 110 to be mounted thereto, and a fixing member 130 configured to fix the magnetic bar block 110 to the magnetic bar block holder 120.

Figure 2:
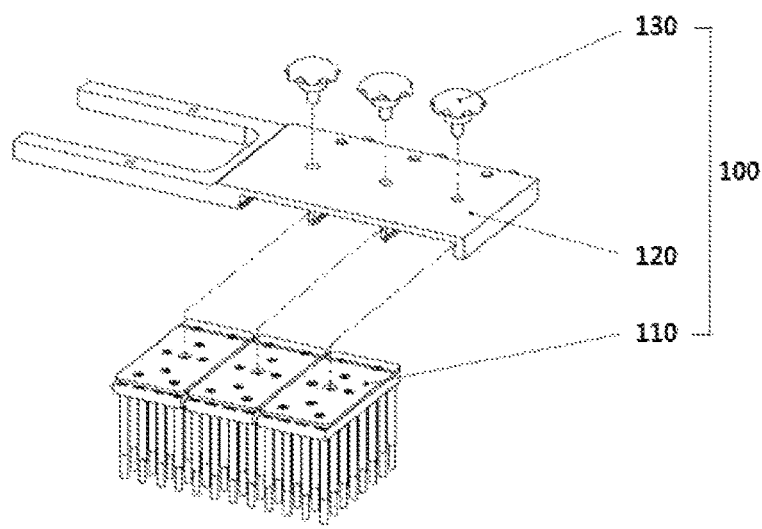
FIG. 2 is a view illustrating a method of installing a magnetic bar block replacement unit 100 according to an embodiment of the present invention.

In the present invention, as shown in FIG. 2, the magnetic bar block replacement unit 100 may be manufactured by fixing the magnetic bar block 110 to the magnetic bar block holder 120 using the fixing member 130. However, as another embodiment, fixing the magnetic bar block 110 can be fixed to the magnetic bar block holder 120 by a male-female coupling type.

Figure 3:
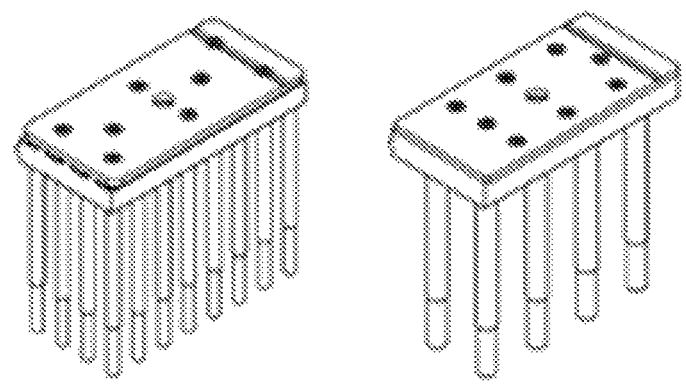
FIG. 3 is a perspective view of a magnetic bar block 110 according to an embodiment of the present invention.

In the present invention, as shown in FIG. 3, the magnetic bar block 110 is configured to have a shape in which a plurality of magnetic bars is attached to the lower surface of a plate. The present invention is characterized in that the number of magnetic bars is equal to the number of wells formed in a multi-well plate containing samples to be extracted using the magnetic bar block 100.

The magnetic bar block 110 may exist in various forms having different numbers of magnetic bars so as to be replaceable depending on the kind of a multi-well plate inserted into a cartridge mounted in a single apparatus for extracting target material together therewith. For example, three magnetic bar blocks, each of which has 32 magnetic bars attached thereto, may be connected to each other so as to be applicable to a 96-well plate, two magnetic bar blocks, each of which has 32 magnetic bars attached thereto, may be provided for a 64-well plate, one magnetic bar block having the above construction may be provided for a 32-well plate, three magnetic bar blocks, each of which has eight magnetic bars attached thereto, may be provided so as to be applicable to a 24-well plate, two magnetic bar blocks, each of which has eight magnetic bars attached thereto, may be provided so as to be applicable to a 16-well plate, or a magnetic bar block having eight magnetic bars applicable to an 8-well plate attached thereto may be manufactured such that the magnetic bar block (s) can be replaced and used depending on the kind of a plate to be used. However, the present invention is not limited as to a magnetic bar block connection mode.

Figure 4:
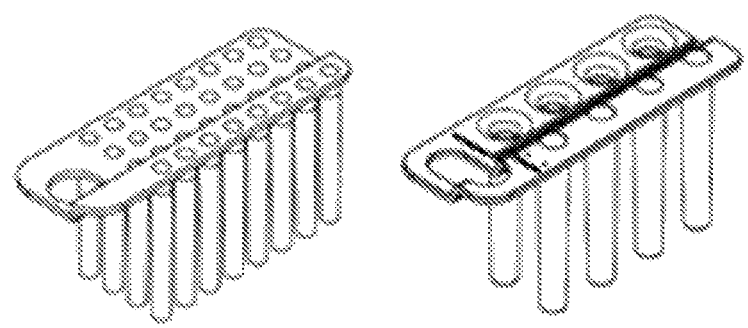
FIG. 4 is a perspective view of a magnetic bar cover block 140 according to an embodiment of the present invention.

Meanwhile, as shown in FIG. 4, the magnetic bar block replacement unit 100 may further include a magnetic bar cover block 140 fastened outside the magnetic bars 111 of the magnetic bar block 110 in order to prevent contamination of the magnetic bars 111.

In the present invention, that the magnetic bar cover block 140 is fastened outside the magnetic bars 111 of the magnetic bar block 110 means that the magnetic bar cover block 140 is fixed so as to surround the entirety or a portion of the surface of each of the magnetic bars 111 of the magnetic bar block 110 in order to prevent the magnetic bars 111 of the magnetic bar block 110 from being contaminated as the result of contacting samples. In the present invention, the magnetic bar cover block 140 is preferably manufactured so as to be disposable, and may be made of various materials suitable to be disposable, such as plastic.

Figure 5:
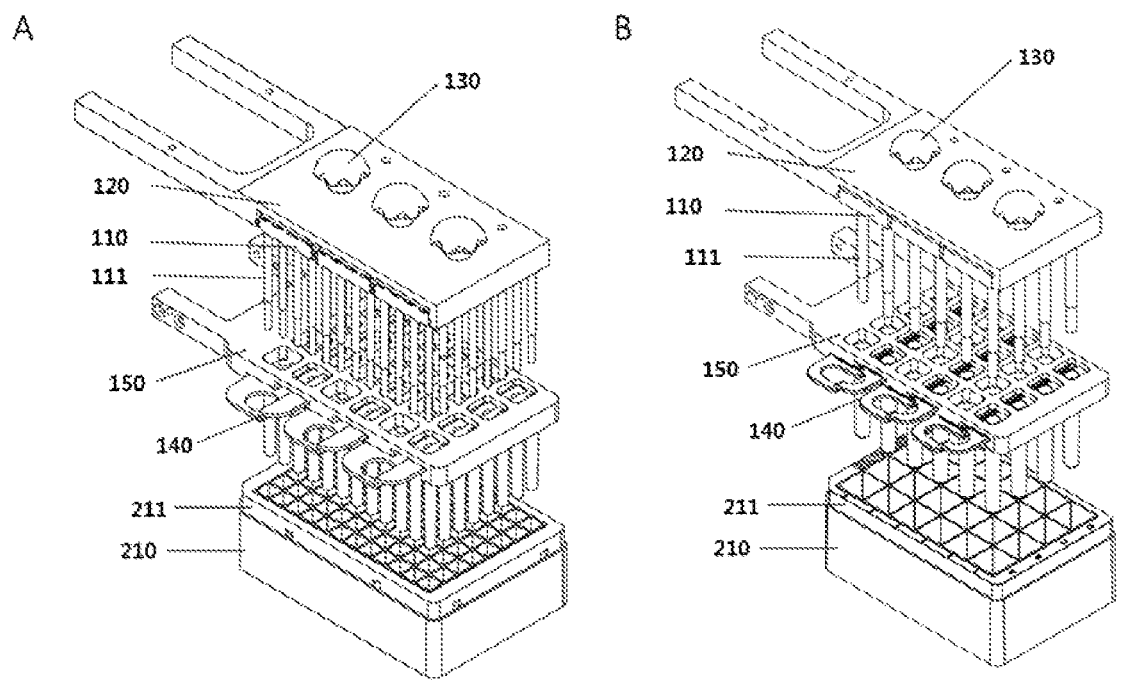
FIG. 5 is a view illustrating a method of installing a magnetic bar block replacement unit 100 suitable for a 96-well plate (A) or a 24-well plate (B) according to another embodiment of the present invention.
Figure 6:
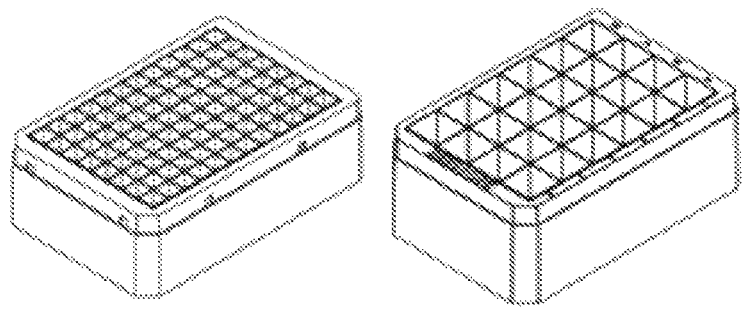
FIG. 6 is a perspective view of a cartridge 210 according to an embodiment of the present invention.

In an aspect of the present invention, the present invention is characterized in that the magnetic bar cover block 140 is fixed to a magnetic bar cover block holder 150, wherein the magnetic bar cover block 140 and the magnetic bar cover block holder 150 are fixed to each other through male-female coupling therebetween or wherein the magnetic bar cover block 140 is fixed to the magnetic bar cover block holder 150 using a fixing member 1302. In another aspect of the present invention, the present invention is characterized in that the magnetic bar cover block 140 is fixed to the magnetic bar block holder 120, which is provided to fix the magnetic bar block 110, wherein the magnetic bar cover block 140 is fixed to the magnetic bar block holder 120 using a fixing member other than the fixing member 130, which is used to fix the magnetic bar block 110 to the magnetic bar block holder 120 (FIG. 5).

In addition, the present invention is characterized in that the magnetic bar block 110 and the magnetic bar cover block 140 are detachable, wherein the magnetic bar block and the magnetic bar cover block are replaced with a magnetic bar block 110 having a different number of magnetic bars attached thereto and a magnetic bar cover block 140 having a different number of magnetic bar covers attached thereto, which are mounted to the magnetic bar block holder 120 or the magnetic bar cover block holder 150, depending on purpose.

Meanwhile, the present invention is characterized in that the cartridge mounting unit 200 is configured such that a plurality of cartridges 210, into each of which a multi-well plate can be inserted, is stacked up and down in the state of being mounted to a cartridge transfer tray 220.

The multi-well plate may be a 96-well plate, a 64-well plate, a 32-well plate, a 24-well plate, a 16-well plate, or an 8-well plate, and may be appropriately selected and applied depending on the number of samples to be extracted or the amount of a target material to be extracted. In another aspect of the present invention, each of the cartridges 210 may be manufactured in the form of a multi-well plate such that the cartridges are stacked up and down in the state of being mounted to the cartridge transfer tray 220 without insertion of separate multi-well plates.

The present invention is characterized in that each of the magnetic bar block 110 and the magnetic bar cover block 140 has the same number of magnetic bars as the number of wells of the mounted multi-well plate.

The present invention is characterized in that the fixing member 130 or other fixing member, which is a means for fixing the magnetic bar block 110 or the magnetic bar cover block 140 to the magnetic bar block holder 120 or the magnetic bar cover block holder 150, respectively, is a fastening means, such as a permanent magnet, an electromagnet, a vacuum suction member, pliers, a jig, a bolt, a pin, a snap ring, a ball plunger, or a combination thereof. In the case in which the above means is used, the fixing member used in the present invention may be manufactured so as to fix or detach the magnetic bar block 110 or the magnetic bar cover block 140 to or from the magnetic bar block holder 120 or the magnetic bar cover block holder 150 without a separate tool or equipment. The present invention is characterized in that the fixing member 130 or other fixing member is adopted at correct positions of the magnetic bar block 110 or the magnetic bar cover block 140 and the magnetic bar block holder 120 or the magnetic bar cover block holder 150 in order to perform coupling therebetween such that the magnetic bar block 110 or the magnetic bar cover block 140 is fixed to a correct position of the magnetic bar block holder 120 or the magnetic bar cover block holder 150, respectively, and the fixed position thereof is not changed under any conditions.

The present invention is characterized in that the target material is nucleic acid. However, the present invention is not limited thereto. Any material capable of being extracted using magnetic particles and magnetic bars, including protein, is applicable without limitation.

DESCRIPTION OF REFERENCE NUMERALS

100: Magnetic bar block replacement unit
110: Magnetic bar block
111: Magnetic bars
120: Magnetic bar block holder
130: Fixing member
130, 130': Fixing members
140: Magnetic bar cover block
150: Magnetic bar cover block holder
200: Cartridge mounting unit
210: Cartridge 211: Multi-well plate
220: Cartridge transfer tray Although specific configurations of the present invention have been described in detail, those skilled in the art will appreciate that preferred embodiments are given for illustrative purposes in the description and should not be construed as limiting the scope of the present invention. Therefore, the substantial scope of the present invention is defined by the accompanying claims and equivalents thereto.

INDUSTRIAL AVAILABILITY

In the case in which the apparatus for extracting target material according to the present invention is used, a multi-well plate suitable for purpose of use, among various kinds of multi-well plates having different numbers of wells, is mounted in a cartridge in the apparatus, and a magnetic bar block having magnetic bars suitable therefor is selected and mounted, whereby it is possible to selectively apply various kinds of multi-well plates to one piece of equipment depending on the number of samples from which a target material is to be extracted or the amount of the target material to be extracted.

The invention claimed is:

1. An apparatus for extracting a target material comprising
   (A) a magnetic bar block replacement unit comprising:
      (i) a magnetic bar block having a plurality of magnetic bars configured to be introduced into each well of a multi-well plate;
      (ii) a magnetic bar block holder configured to allow the magnetic bar block to be mounted thereto;
      (iii) a fixing member configured to fix the magnetic bar block to the magnetic bar block holder; and
      (iv) a magnetic bar cover block fastened outside the magnetic bars of the magnetic bar block, the magnetic bar cover block being configured to prevent contamination of the magnetic bars, wherein the magnetic bar cover block is mounted to a magnetic bar cover block holder, and wherein the magnetic bar cover block and the magnetic bar cover block holder are fixed to each other through male female coupling therebetween; and
   (B) a cartridge mounting unit configured such that a plurality of cartridges, into each of which a multi-well plate can be inserted, is stacked, in which each cartridge is mounted to a cartridge transfer tray.

2. The apparatus for extracting a target material according to claim 1, wherein the magnetic bar block and the magnetic bar cover block are detachable.

3. The apparatus for extracting a target material according to claim 1, wherein the multi-well plate is a 96-well plate, a 64-well plate, a 32-well plate, a 24-well plate, a 16-well plate, or an 8-well plate.

4. The apparatus for extracting a target material according to claim 1, wherein each of the magnetic bar block and the magnetic bar cover block has an identical number of magnetic bars to a number of wells of the mounted multi-well plate.

5. The apparatus for extracting a target material according to claim 1, wherein the fixing member is a fastening means of a permanent magnet, an electromagnet, a vacuum suction member, pliers, a jig, a bolt, a pin, a snap ring, a ball plunger, or a combination thereof.

6. The apparatus for extracting a target material according to claim 1, wherein the target material is nucleic acid.

* * * * *

UNITED STATES PATENT AND TRADEMARK OFFICE
CERTIFICATE OF CORRECTION

PATENT NO. : 12,012,592 B2
APPLICATION NO. : 17/262796
DATED : June 18, 2024
INVENTOR(S) : Han-Oh Park et al.

Page 1 of 1

It is certified that error appears in the above-identified patent and that said Letters Patent is hereby corrected as shown below:

On the Title Page

Item (57) Abstract, Lines 8-9, "various plates multi-well" should be -- various multi-well plates --.

In the Specification

Column 2, Line 37, "a tube a uniform" should be -- a tube using a uniform --.

Column 5, Line 55, "fixing member 1302" should be -- fixing member --.

Column 6, Line 63, "130, 130': Fixing members" should be -- 130: Fixing member --.

Signed and Sealed this
Sixth Day of August, 2024

Katherine Kelly Vidal
*Director of the United States Patent and Trademark Office*